United States Patent
Umeda et al.

[11] Patent Number: 5,877,311
[45] Date of Patent: *Mar. 2, 1999

[54] PROCESS FOR ISOMERIZATION OF COMPOUND OF ALDOSE STRUCTURE INTO COMPOUND OF KETOSE STRUCTURE, AND ISOMERIZATION AGENT OR ACCELERATOR USED THERIN

[75] Inventors: Keiji Umeda, Ibaraki; Norihiro Kakimoto, Tokyo; Takafumi Kasumi, Ibaraki, all of Japan

[73] Assignees: National Food Research Institute, Ministry of Agriculture, Forestry & Fisheries, Ibaraki; Asai Germanium Research Institute Co., Ltd., Tokyo, both of Japan

[ * ] Notice: The term of this patent shall not extend beyond the expiration date of Pat. No. 5,679,787.

[21] Appl. No.: 888,285

[22] Filed: Jul. 3, 1997

Related U.S. Application Data

[63] Continuation of Ser. No. 295,739, Oct. 25, 1994, Pat. No. 5,679,787.

[30] Foreign Application Priority Data

Aug. 25, 1994 [WO] WIPO ........................ PCT/JP93/01896

[51] Int. Cl.$^6$ .............................. C07H 1/00; C01G 17/00
[52] U.S. Cl. ......................... 536/125; 536/18.5; 536/124; 423/618
[58] Field of Search .................................. 536/18.5, 124, 536/125; 423/618

[56] References Cited

U.S. PATENT DOCUMENTS

| | | | |
|---|---|---|---|
| 4,066,678 | 1/1978 | Sato et al. | 260/429 R |
| 4,069,104 | 1/1978 | Barker et al. | 195/31 F |
| 4,133,696 | 1/1979 | Barker et al. | 127/46 A |
| 5,006,553 | 4/1991 | Kakimoto et al. | 514/492 |

FOREIGN PATENT DOCUMENTS

| | | |
|---|---|---|
| 834 794 | 2/1976 | Belgium . |
| 2 316 246 | 1/1977 | France . |
| 2 622 443 | 5/1988 | France . |

OTHER PUBLICATIONS

Chemical Abstracts, vol. 94, No. 17, 26 Oct. 1981, p. 962, 'Organogemanium Compounds'.
Chemical Abstracts, vol. 108 No. 5, 1 Feb. 1988, page 652, 'Organogermanium Compounds'.
Chemical Abstracts, vol. 117, No. 5, 3 Aug. 1992, page 972, Preparation of Optically Active 'Organogermanium Compounds'.

Primary Examiner—Howard C. Lee
Attorney, Agent, or Firm—Burns, Doane, Swecker & Mathis, L.L.P.

[57] ABSTRACT

A process is provided which comprises isomerizing a compound having a ketose structure by the use of or in the presence of an organogermanium compound having a structural portion represented by formula (I):

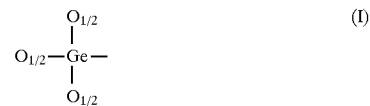

Due to the use or presence of the organogermanium compound, the process is free from the problems of the prior art, and is capable of isomerizing a compound having an aldose structure into a compound having a ketose structure at a high isomerization ratio without requiring any special apparatus or any complicated operation.

20 Claims, 1 Drawing Sheet

Fig. 1

PROCESS FOR ISOMERIZATION OF COMPOUND OF ALDOSE STRUCTURE INTO COMPOUND OF KETOSE STRUCTURE, AND ISOMERIZATION AGENT OR ACCELERATOR USED THERIN

This application is a continuation of application Ser. No. 08/295,739, filed Oct. 25, 1994, now U.S. Pat. No. 5,679,787.

TECHNICAL FIELD

The present invention relates to a process for isomerizing a compound having an aldose structure into a compound having a ketose structure, as well as to an isomerization agent or accelerator used in said process.

BACKGROUND ART

Carbohydrates are organic compounds which are very important to living things as their energy sources, etc. and which are present most abundantly on the earth. They are composed mainly of monosaccharides. These monosaccharides have typical structures in which 3 to 8 carbon atoms are bonded in a ring and the structures are largely classified into two types.

That is, said structures are classified into aldose (an aldehyde-containing monosaccharide) and ketose (a ketone-containing monosaccharide). Both aldose and ketose are further classified into respective trioses, tetroses, pentoses and hexoses depending upon the carbon atom number of aldose or ketose.

Various reactions using monosaccharides are known. As such a reaction which is used industrially, there is a reaction which comprises isomerizing glucose (grape sugar) (an aldohexose) into fructose (fruit sugar) (a corresponding ketohexose) to produce a high-fructose syrup.

Said high-fructose syrup is a mixture of glucose and fructose, obtained by isomerizing glucose partially. Owing to the partial isomerization of glucose (having low sweetness) into fructose (having high sweetness), the high-fructose syrup has sweetness similar to that of sucrose.

About 70% of the high-fructose syrup is used in cooling drinks and other drinks because fructose contained therein has higher sweetness at lower temperatures, and other portion is used in general foodstuffs as a sweetener. The yearly production of high-fructose syrup in the world is estimated about 8,000,000 kg.

Both glucose and fructose are hexoses similar in structure. Chemical and enzymatic processes have hitherto been proposed for isomerization of glucose into fructose, and it is currently conducted in industry to isomerize glucose into fructose using an isomerization enzyme, namely, glucose isomerase to produce a high-fructose syrup.

That is, starch, for example, corn starch is liquefied; the resulting liquid is subjected to saccharification using glucoamylase to obtain a starch syrup; and passing the starch syrup continuously through an immobilized enzyme obtained by immobilizing, using one of various methods, a glucose isomerase produced by, a microorganism of, for example, Streptomyces genus, to isomerize the glucose contained in said solution into fructose.

The above isomerization reaction is an equilibrium reaction whose equilibrium point is 1 or thereabouts. At the equilibrium point, about 50% of glucose can be isomerized into fructose at a reaction temperature of about 60° C. In order to allow the isomerization to proceed to such a level, however, a considerable length of time is required, the reaction mixture is colored owing to the heating for such a long time, and a high cost is incurred for the purification and condensation steps required for product marketing. Hence, the reaction is terminated when the isomerization has proceeded to a fructose content of about 42%.

As described above, the high-fructose syrup is produced in order to allow glucose of mass production and low cost to have sweetness similar to that of sucrose. However, when the sweetness of sucrose is arbitrarily taken as 100, the above-mentioned high-fructose syrup containing about 42% of fructose (this fructose syrup is hereinafter referred to as 42%-fructose syrup, in some cases) has a sweetness of 95–100 which is slightly insufficient. Therefore, in the above isomerization reaction alone, it is impossible to directly obtain a high-fructose syrup having the same sweetness as sucrose.

Hence, there is currently produced in industry a 55%-fructose syrup having a sweetness of 100–110 by increasing the fructose content in the 42%-fructose syrup to 55%.

In order to produce a 55%-fructose syrup from the 42%-fructose syrup, however, a large apparatus such as a reactor packed with a cation exchange resin is required; moreover, a complicated operation must be conducted, that is, continuous sugar separation is conducted using said reactor to obtain a fructose syrup containing about 95% of fructose and then this fructose is mixed with the 42%-fructose syrup.

Meanwhile, as the isomerization of other compound having an aldose structure into a compound having a ketose structure, there can be mentioned, for example, isomerization of lactose (a disaccharide) into lactulose. In this isomerization, however, unlike the above isomerization of glucose into fructose, no enzyme effective for isomerization of lactose into lactulose has not yet been found; therefore, the isomerization is currently conducted by adding, to lactose, sodium hydroxide of a concentration not exceeding a given level and then heating the mixture at 70° C. or higher to isomerize lactose into lactulose (Japanese Patent Publication No. 2984/1977). This process, however, gives a low isomerization ratio, i.e. a low lactulose yield of 20% or less (this is lower than the fructose yield). In order to obtain a high-lactulose syrup, the process has a problem that the lactulose syrup obtained must be condensed.

An object of the present invention is to provide a process which is free from the above-mentioned problems of prior art and which can isomerize a compound having an aldose structure into a compound having a ketose structure at a high isomerization ratio.

Another object of the present invention is to provide a process which can isomerize a compound having an aldose structure into a compound having a ketose structure without requiring any special apparatus or any complicated operation.

Still another object of the present invention is to provide a process which can isomerize a compound having an aldose structure into a compound having a ketose structure, using an isomerization enzyme or without using any isomerization enzyme.

Still another object of the present invention is to provide a process which can isomerize a compound having an aldose structure into a compound having a ketose structure without employing the condition of heating in alkalinity (this condition is sometimes disadvantageous for isomerization ratio) even when there has been found no enzyme effective for said isomerization.

Still another object of the present invention is to provide an isomerization agent or accelerator effective in the above process.

DISCLOSURE OF THE INVENTION

According to the present invention there is provided a process which comprises isomerizing a compound having an aldose structure into a compound having a ketose structure, by the use of or in the presence of an organogermanium compound having a structural portion represented by the following formula (I).

According to the present invention there is further provided an isomerization agent or accelerator effective for the isomerization of a compound having an aldose structure into a compound having a ketose structure, which agent or accelerator comprises, as an active component, an organogermanium compound having a structural portion represented by the following formula (I).

BRIEF DESCRIPTION OF THE DRAWING

Δ: A case where an organogermanium compound (23) was used as the present isomerization agent.

◇: A case where an organogermanium compound (18) was used as the present isomerization agent.

☐: A case where an organogermanium compound (1) was used as the present isomerization agent.

○: A blank

PREFERRED EMBODIMENTS OF THE INVENTION

The present invention is hereinafter described in detail.

In the present invention, the isomerization of a compound having an aldose structure into a compound having a ketose structure is conducted by the use of or in the presence of an organogermanium compound having a structural portion represented by the above-mentioned formula (I) with the remaining structure being a chain or cyclic hydrocarbon, a substitution product or derivative thereof, or other organic group. Hence, description is made first on the organogermanium compound having such a structure.

The organogermanium compound can be exemplified by a compound represented by formula (II)

[$R_1$, $R_2$ and $R_3$, which may be the same or different, independently represent a hydrogen atom, a lower alkyl group, a substituted or unsubstituted phenyl group, a carboxyl group, a carboxyalkyl group or an amino group which is unsubstituted or substituted with appropriate group(s); $X_1$ represents a hydroxyl group, an O-lower alkyl group, an amino group or a salt represented by $OY_1$ ($Y_1$ represents a metal or a basic group-containing compound); and n represents an integer of 1 or more], which contains, as a basic skeleton, a germylcarboxylic acid derivative formed by bonding between a germanium atom and a carboxylic acid derivative having three substituents $R_1$, $R_2$ and $R_3$ and an oxygen-containing functional group $OX_1$, with the germanium atom in the basic skeleton bonding to oxygen atoms at an atomic ratio of 2 (germanium):3 (oxygen).

The substituents $R_1$, $R_2$ and $R_3$, which may be the same or different, independently represent a hydrogen atom; a lower alkyl group such as methyl, ethyl, propyl, butyl or the like; a substituted or unsubstituted phenyl group; a carboxyl group; a carboxyalkyl group; or an amino group which is unprotected or protected with a protective group such as acetyl or the like. The substituent $X_1$ represents a hydroxyl group, an O-lower alkyl group, an amino group or a salt represented by $OY_1$ [$Y_1$ represents a metal such as sodium, potassium or the like (the metal need not be monovalent), or a basic compound typified by lysozyme or a basic amino acid such as lysine].

The substituents $R_1$ and $R_2$ bond to each carbon of the carbon chain represented by $(C)_n$ (n is an integer of 1 or more) present at the α-position of the germanium atom. Accordingly, when n is 1, 2, ... n, $R_1$ becomes $R_{11}$, $R_{12}$, ... $R_{1n}$, and $R_{2n}$ becomes $R_{21}$, $R_{22}$, ... $R_{2n}$. The substituent $R_3$ bonds to the methylene group present between said carbon chain and the oxygen-containing functional group.

The organogermanium compound used in the present invention can therefore be exemplified by those shown in the following Tables 1–5.

TABLE 1

| Compound No. | R1<br>\|<br>(C)n<br>\|<br>R2 | R3 | X1 |
|---|---|---|---|
| 1 | CH2 | H | OH |
| 2 | CH3<br>\|<br>CH | H | OH |
| 3 | CH2 | CH3 | OH |
| 4 | CH3<br>\|<br>CH | CH3 | OH |
| 5 | CH3<br>\|<br>C<br>\|<br>CH3 | H | OH |
| 6 | C6H5<br>\|<br>CH | H | OH |
| 7 | C6H5<br>\|<br>CH | CH3 | OH |
| 8 | CH2 | CH2COOH | OH |
| 9 | C6H5<br>\|<br>CH | CH2COOH | OH |
| 10 | CH2 | H | ONa |

TABLE 2

| Compound No. | R1\|(C)n\|R2 | R3 | X1 |
|---|---|---|---|
| 11 | CH2 | H | NH2 |
| 12 | CH3\|CH | H | NH2 |
| 13 | CH2 | CH3 | NH2 |
| 14 | CH3\|CH | CH3 | NH2 |
| 15 | CH3\|C\|CH3 | H | NH2 |
| 16 | C6H5\|CH | H | NH2 |
| 17 | C6H5\|CH | CH3 | NH2 |

TABLE 3

| Compound No. | R1\|(C)n\|R2 | R3 | X1 |
|---|---|---|---|
| 18 | CH2 | NH2 | OH |
| 19 | CH3\|CH | NH2 | OH |
| 20 | CH3\|C\|CH3 | NH2 | OH |
| 21 | CH3\|CH | NH2 | OCH3 |
| 22 | CH3\|C\|CH3 | NH2 | OCH3 |
| 23 | C6H5\|CH | NH2 | OH |
| 24 | C6H5\|CH | NH2 | OCH3 |
| 25 | CH2 | NH2 | OCH3 |
| 26 | CH2 | NH2 | ONa |

TABLE 4

| Compound No. | R1\|(C)n\|R2 | R3 | X1 |
|---|---|---|---|
| 27 | CH2 | NHCOCH3 | OH |
| 28 | CH3\|CH | NHCOCH3 | OH |
| 29 | CH3\|CH2\|CH3 | NHCOCH3 | OH |
| 30 | CH3\|CH | NHCOCH3 | OCH3 |
| 31 | CH3\|C\|CH3 | NHCOCH3 | OCH3 |
| 32 | C6H5\|CH | NHCOCH3 | OH |
| 33 | C6H5\|CH | NHCOCH3 | OCH3 |
| 34 | CH2 | NHCOCH3 | OCH3 |
| 35 | CH2 | NHCOCH3 | ONa |

TABLE 5

| Compound No. | $R_1$\|$(C)_n$\|$R_2$ | $R_3$ | $X_1$ |
|---|---|---|---|
| 36 | $CH_2CH_2$ | H | OH |
| 37 | $CH_3$\|$CHCH_2$ | H | OH |
| 38 | $CH_3$\|$CH_2CH$ | H | OH |
| 39 | $CH_2CH_2$ | $CH_3$ | OH |
| 40 | $C_6H_5$\|$CHCH_2$ | H | OH |
| 41 | $CH_2CH_2$ | $NH_2$ | OH |
| 42 | $CH_2CH_2$ | H | $NH_2$ |
| 43 | $CH_2CH_2$ | $NHCOCH_3$ | OH |
| 44 | $CH_2CH_2CH_2$ | H | OH |
| 45 | $CH_3$\|$CHCH_2CH_2$ | H | OH |
| 46 | $CH_3$\|$CH_2CHCH_2$ | H | OH |
| 47 | $CH_2CH_2CH_2$ | $CH_3$ | OH |
| 48 | $C_6H_5$\|$CHCH_2CH_2$ | H | OH |

TABLE 5-continued

| Compound No. | $\begin{array}{c}R_1\\|\\(C)_n\\|\\R_2\end{array}$ | $R_3$ | $X_1$ |
|---|---|---|---|
| 49 | $CH_2(CH_2)_2CH_2$ | H | OH |
| 50 | $\begin{array}{c}CH_3\\|\\CH(CH_2)_2CH_2\end{array}$ | H | OH |
| 51 | $CH_2(CH_2)_3CH_2$ | H | OH |

Of the compounds shown in Tables 1–5, those shown in Tables 1–4 represented by the following formula (III) are preferable from the availability standpoint:

wherein $R_4$, $R_5$ and $R_6$, which may be the same or different, independently represent, similarly to $R_1$, $R_2$ and $R_3$, a hydrogen atom, a lower alkyl group, a substituted or unsubstituted phenyl group, a carboxyl group, a carboxyalkyl group or an amino group which is unsubstituted or substituted with appropriate group(s); and $X_2$ represents, similarly to $X_1$, a hydroxyl group, an O-lower alkyl group, an amino group or a salt represented by $OY_2$ ($Y_2$ represents a metal or a basic group-containing compound).

The organogermanium compound having the above structure can be produced by various methods (for example, Japanese Patent Publication No. 40159/1984, Japanese Patent Kokai (Laid-open) No. 86890/1991 and Japanese Patent Kokai (Laid-open) No. 62885/1990). Description is made on the production of organogermanium compounds represented by formula (III).

An organogermanium compound of formula (III) wherein $X_2$ is a hydroxyl group, can be produced by, for example, hydrolyzing a trihalogermylpropionic acid (e.g., trichlorogermylpropionic acid) having substituents $R_4$ to $R_6$, as shown in the following formula.

An organogermanium compound of formula (III) wherein $X_2$ is an O-lower alkyl group, can be produced by, for example, reacting the above trichlorogermylpropionic acid with thionyl chloride or the like to convert said acid into a corresponding acid halide, reacting said halide with an alcohol corresponding to said lower alkyl group, and hydrolyzing the reaction product. An organogermanium compound of formula (III) wherein $X_2$ is an amino group, can be produced by, for example, reacting said acid halide with ammonia and then hydrolyzing the reaction product.

An organogermanium compound of formula (III) wherein $X_2$ is a salt represented by $OY_2$ and $Y_2$ is a metal, can be produced by reacting a compound of formula (III) wherein $X_2$ is a hydroxyl group, with a hydroxide of $Y_2$. An organogermanium compound of formula (III) wherein $X_2$ is a salt represented by $OY_2$ and $Y_2$ is a basic group-containing compound, can be synthesized by a known acid-base reaction.

Organogermanium compounds of formula (III) wherein n is larger than 1, can be produced basically in accordance with the above-mentioned methods.

That the thus produced organogermanium compound is represented by the above-shown general formula (II) can be well supported by the results of instrumental analyses (e.g., NMR absorption spectrum, IR absorption spectrum) obtained for said compound.

The formulas (II) and (III) representing the organogermanium compound of the present invention, each represents said compound in its crystal state. It is known that the present compound, for example compound (II), takes a structure represented by the following formula (II'), in water.

The organogermanium compounds (II) and (III) can be represented also by other structural formulas. For example, the compound (II) is the same as a compound represented by the following structural formula (II'').

In the present invention, the organogermanium compound which is represented by at least one of above formulas can be used, regardless of their crystal structures.

The organogermanium compound used in the present invention has very low toxicity. For example, a compound (II) wherein n=1, $R_1=R_2=R_3=H$ and $X_1=OH$ [compound No. 1, this compound is hereinafter referred to as organogermanium compound (1) in some cases], shows a $LD_{50}$ of 6 g/kg or more when orally administered to mice and 10 g/kg or more when orally administered to rats.

In the present invention, as described previously, a compound having an aldose structure is isomerized into a compound having a ketose structure by the use of or in the presence of an organogermanium compound having a structural portion represented by the above formula (I). The compound to be isomerized may be any compound which has, in the molecule, the following aldose structure represented by Fischer's projection formula and which can be isomerized into a compound having the following ketose structure represented by Fischer's projection formula via an interim stage of formation of a cis-ene-diol structure as shown below.

As the compound having the above aldose structure, monosaccharides and their derivatives such as shown below at the left side can be mentioned. They are isomerized into compounds shown below at the right side.

glyceraldehyde→dihydroxyacetone
erythrose, threose→erythrulose
ribose, arabinose→ribulose
xylose, lyxose→xylulose
allose, altrose→psicose
glucose, mannose→fructose
gulose, idose→sorbose
galactose, talose→tagatose As the compound having the aldose structure, reducing disaccharides and their derivatives such as shown below at the left side can also be mentioned. They are isomerized into compounds shown below at the right side.

maltose→maltulose
lactose→lactulose

Trisaccharides and higher, and also polysaccharides and their derivatives can be isomerized. In that case, they must have an aldose structure at the molecular end. Incidentally, for some (e.g. maltose and lactose) of the above compounds which can be isomerized, there has been found no enzyme capable of isomerizing them into corresponding compounds each having a ketose structure.

Of the compounds of ketose structure, lactulose is clinically used for the improvement of psychoneurosis associated with hyperammonemia, tremors of hands and fingers, etc.

In the isomerization of a compound having an aldose structure according to the present invention, an isomerization enzyme may or may not be used. When no isomerization enzyme is used, the isomerization may be conducted under the same conditions as employed in the conventional isomerization of glucose into fructose using an isomerization enzyme, for example, at room temperature to 60°–90° C. in the presence of an alkali such as sodium hydroxide, calcium hydroxide or the like. In the isomerization using no enzyme, it is also possible to use the alkaline portion of the electrolytic water obtained by the polarization of water using a particular apparatus therefor.

The concentration of the organogermanium compound used in the isomerization are not particularly restricted because it is determined depending upon isomerization time, desired isomerization ratio, etc. However, as an example, 1% by weight or more of the organogermanium compound is added to a 10% by weight to solution of the compound having an aldose structure.

In the isomerization of the present process, the isomerization ratio increases generally with an increase in the reaction time. Therefore, the isomerization ratio is controlled by controlling the reaction time, whereby a desired isomerization ratio is obtained.

In the isomerization process according to the present invention, an isomerization enzyme may be used as in the conventional isomerization of glucose into fructose using an isomerization enzyme.

Description is made on a case of isomerization of glucose into fructose using an isomerization enzyme. First, starch (e.g. corn starch) is liquefied using α-amylase produced by, for example, Bacillus genus; the resulting liquid is subjected to saccharification using glucoamylase produced by, for example, Aspergillus niger, to obtain a starch syrup. Incidentally, this starch syrup contains about 93–95% of glucose. In the saccharification, there may be used, in combination, pullulanase which is an enzyme for cleavage of α-1,6-glycoside linkage of starch; in this case, the glucose content in the resulting starch syrup is about 96%.

The starch syrup is purified and condensed as necessary; then, there is added, as necessary, a metal ion of magnesium, manganese or cobalt required by glucose isomerase used in the subsequent isomerization step. From the standpoint of food safety, magnesium ion is preferred as the metal ion.

The resulting starch syrup is subjected to an isomerization step. Glucose isomerase used in this step maybe any as long as it can isomerize glucose into fructose. Examples of glucose isomerase are those enzymes produced by microorganisms belonging to Streptomyces genus, Bacillus genus, Arthrobacter genus, Microbacterium genus, etc. Specific examples of the enzyme are as follows.

*Lactobacillus brevis*
*Bacillus coagulans*
*Brevibacterium pentosoaminoacidium*
*Arthrobactor sp.*
*Actinoplanes missouriensis*
*Streptomyces phaeochromogenus*
*Streptomyces rubiginosus*
*Streptomyces albus* NRRL-5778
*Streptomyces griseofuscus*

The above-mentioned glucose isomerase is allowed to act on the above-mentioned starch syrup in the presence of the above-mentioned organogermanium compound to isomerize glucose in the syrup into fructose. This step may be conducted in a mixture of the starch syrup, the organogermanium compound and the glucose isomerase; however, it is also possible that the glucose isomerase be immobilized according to one of conventional methods to prepare an immobilized enzyme and the starch syrup containing the organogermanium compound be continuously passed through the immobilized enzyme. Incidentally, in the present invention, a microbial cell preparation whose proteins other than glucose isomerase have been inactivated, may be used in place of the isomerization enzyme.

The conditions employed for the isomerization of glucose into fructose according to the present invention, can be the same as used in the conventional known isomerization processes. That is, the isomerization may be conducted, for example, in neutrality to weak alkalinity at 60°–90° C.

In the isomerization of glucose into fructose according to the present invention, the isomerization ratio increases with the lapse of the reaction time, as shown in Examples given later. Therefore, it is possible to control the reaction time to control the isomerization ratio and thereby obtain a desired isomerization ratio, for example, a ratio of isomerization to fructose of about 55% or more.

In the present invention, the amount of the organogermanium compound used can be determined depending upon the intended isomerization ratio, etc. The organogermanium compound can be used in a concentration range of, for example, 1/100M or more.

The present invention is hereinafter described in more detail with reference to Examples.

EXAMPLE 1
(1) Synthesis of Organogermanium Compounds

Trichlorogermane ($Cl_3GeH$) was added to acrylic acid ($CH_2CHCOOH$) to obtain trichlorogermylpropionic acid ($Cl_3GeCH_2CH_2COOH$). It was hydrolyzed to synthesize an organogermanium compound (1). In the same manner were synthesized organogermanium compounds (2) to (51).

(2) Preparation of Substrate Solutions

A solution containing 40% glucose and 1.2M organogermanium compound was prepared according to the following procedure. 0.8 g of anhydrous glucose was dissolved in 0.8 ml of deionized water. To the solution was added, in small portions, 0.407 g of the organogermanium compound (1) as an isomerization accelerator of the present invention [a compound represented by formula (II) wherein n=1, $R_1=R_2=R_3$ and $X_1=OH$] while the pH of the solution was maintained at very weak alkalinity, to completely dissolve the compound in the solution. Thereto was added 4.9 mg of magnesium sulfate, and the pH of the resulting mixture was adjusted to 8.0. Then, deionized water was added to make the total volume 2.0 ml, whereby a substrate solution was prepared.

Two other substrate solutions containing the organogermanium compounds (18) [a compound represented by formula (II) wherein n=1, $R_1=R_2=H$, $R_3=NH_2$ and $X_1=OH$] and (23) [a compound represented by formula (II) wherein n=1, $R_1=H$, $R_2=C_6H_5$, $R_3=NH_2$ and $X_1=OH$], respectively, were prepared in the same manner as above except that the organogermanium compounds (18) and (23) were used in amounts of 0.443 g and 0.638 g, respectively (these amounts corresponded to 1.2M of germanium).

(3) Preparation of Enzyme

An isomerization enzyme (glucose isomerase) extracted from the cells of *Streptomyces griseofuscus* S-41 was purified according to a known method using an ion exchange column, a gel filtration column or the like, until a single band was obtained electrophoretically. The resulting purified enzyme was used as a standard enzyme.

(4) Enzymatic Isomerization Reaction

In a small test tube were placed 0.7 ml of the above substrate solution, 0.1 ml of a 200 mM MOPS buffer solution (pH 8.0) and 0.2 ml of a solution containing the above-prepared standard enzyme (5.69 mg/ml). The test tube was placed in a water bath of 60° C. and the mixture in the test tube was subjected to a reaction. Each 50 μl of the reaction mixture was taken and added, at regular intervals, to 50 μl of 0.5N perchloric acid placed in a microvial, to terminate the reaction. The amount of formed fructose in the microvial was determined by high-performance liquid chromatography using a column [LC7A, SCR-101 (N) manufactured by Shimadzu Corp.] to examine the change with time, of ratio of isomerization of glucose into fructose.

(5) Results

Figure 1:
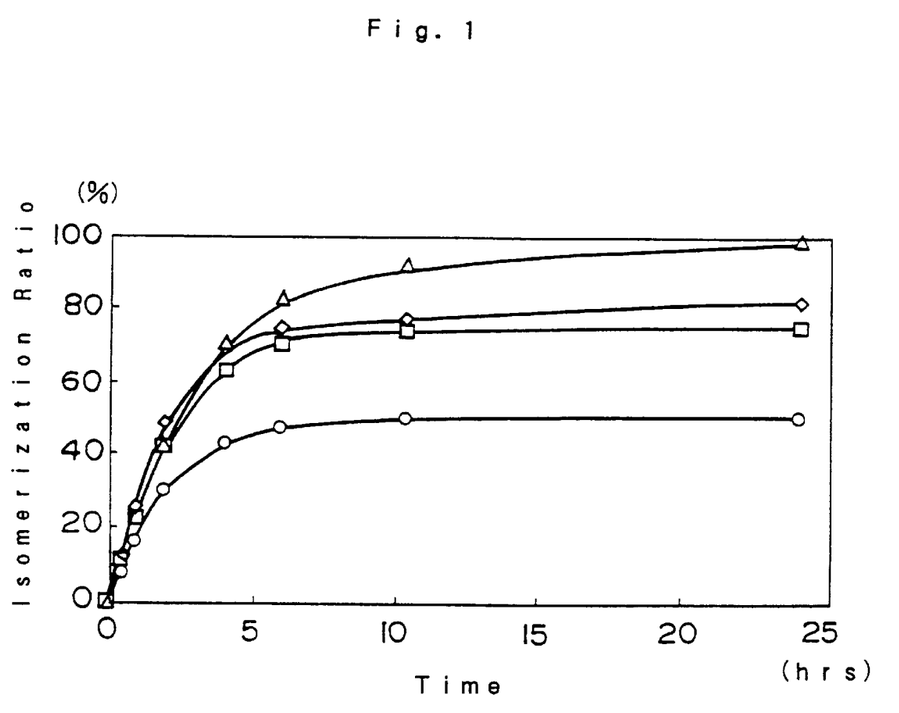
FIG. 1 is a graph showing a relation between reaction time and isomerization ratio.

As shown in FIG. 1, in the blank using no organogermanium compound, the reaction reached an equilibrium in about 6 hours and the isomerization ratio was as low as 50%. When the organogermanium compound of the present invention was added as an isomerization accelerator, both the initial reaction rate and the isomerization ratio in equilibrium were superior to those of the blank. That is, the initial reaction rate was 40–50% higher than that of the blank, in all cases and there was substantially no difference in initial reaction rate between different organogermanium compounds. Meanwhile, the isomerization ratio in equilibrium varied depending upon the kinds of organogermanium compounds used; and the compound (23) gave an isomerization ratio of 99%, the compound (18) gave an isomerization ratio of 80%, and the compound (1) gave an isomerization ratio of 75%.

EXAMPLE 2
(1) Preparation of Weakly Alkaline Electrolytic Water by Electrolysis

Water was passed through an apparatus for electrolysis [e.g. Microcluster (trade name) manufactured by Asahi Glass Co., Ltd.]. The alkaline portion of the resulting electrolytic water was taken to use as a weakly alkaline electrolytic water.

(2) Preparation of Glucose Solutions 14 g or 28 g of anhydrous glucose was dissolved in about 80 ml of the weakly alkaline electrolytic water prepared above. The same electrolytic water was further added to make the total volume 100 ml, whereby a 14% glucose solution and a 28% glucose solution were prepared. The 14% glucose solution had pH 9.1 and the 28% glucose solution had pH 8.61, right after the preparation.

(3) Preparation of Organogermanium Compound Solutions 1.847 g of the organogermanium compound (18) was weighed and added to about 2 ml of deionized water. The mixture was made weakly alkaline (pH 8.00 or 8.53) with a small amount of sodium hydroxide. The same deionized water was further added to make the total volume of 3 ml. The final concentration of the compound (18) in the solution was 1.67M.

(4) Isomerization

200 μl of the 14% or 28% glucose solution and 200 μl of the organogermanium compound solution (pH 8.00 or 8.53) were placed in a small test tube. Also, 200 μl of the 14% or 28% glucose solution and 200 μl of the weakly alkaline electrolytic water were placed in a small test tube. Each test tube was thoroughly shaken and then placed in a water bath of 80° C. to give rise to a reaction. 1–3 hours later, 50 μl of the reaction mixture was added to 50 μl of 0.5N $HClO_4$ to terminate the reaction. Thereafter, the mixture was diluted 100-fold with deionized water to determine the amount of formed fructose and the amount of residual glucose by high-performance liquid chromatography using 7A (a column) manufactured by Shimadzu Corp.

The results are shown in Table 6.

TABLE 6

| Run No. | Glucose concentration (%) | pH of reaction mixture | Isomerization ratio (%) |
|---|---|---|---|
| 1 (Ge) | 14 | 7.17 | 48.0 |
| 2 | 14 | 8.75 | 2.1 |
| 3 (Ge) | 7 | 7.52 | 73.1 |
| 4 | 7 | 9.03 | 3.1 |

TABLE 6-continued

| Run No. | Glucose concentration (%) | pH of reaction mixture | Isomerization ratio (%) |
|---|---|---|---|
| 5 (Ge) | 14 | 7.81 | 65.0 |
| 6 | 14 | 8.74 | 2.0 |
| 7 (Ge) | 7 | 8.15 | 94.7 |
| 8 | 7 | 9.03 | 3.5 |
| 9 (Na, Ge) | 14 | 8.61 | 98.9 |
| 10 (Na) | 14 | 10.62 | 32.3 |

As is clear from Table 6, the isomerization ratios of glucose were 2.0 to 3.5% when a glucose solution was dissolved in a weakly alkaline electrolytic water alone. Meanwhile, when an organogermanium compound solution was further added, the isomerization ratios of glucose were 48.0 to 94.7%. Further, the isomerization ratio of glucose was 32.3% when sodium hydroxide was added to a glucose solution, while the isomerization ratio of glucose was 98.9% when an organogermanium compound solution was further added.

Incidentally, in Table 6, (Ge) shows cases in which an organogermanium compound solution was added; (Na) shows a case using sodium hydroxide and deionized water; in other cases, isomerization was conducted using weakly alkaline electrolytic water alone and without using any of (Ge) and (Na).

EXAMPLE 3

Other compounds represented by formula (I) were subjected to 3-hour isomerization in the same manner as in Example 2. The results are shown in Table 7. Incidentally, compounds other than those shown in Table 7 showed substantially the same isomerization ratios.

TABLE 7

| Formula | Compound No. | Glucose *(1) NaOH | Glucose *(1) Electrolytic water | Mannose *(2) NaOH | Mannose *(2) Electrolytic water | Arabinose *(2) NaOH | Arabinose *(2) Electrolytic water | Ribose *(2) NaOH | Ribose *(2) Electrolytic water | Xylose *(2) NaOH | Xylose *(2) Electrolytic water | Lactose *(3) NaOH | Lactose *(3) Electrolytic water | Maltose *(3) NaOH | Maltose *(3) Electrolytic water |
|---|---|---|---|---|---|---|---|---|---|---|---|---|---|---|---|
| Ge―\―COOH | 1 | 98.9 | 94.7 | 24.3 | 13.1 | 22.6 | 12.6 | 44.7 | 33.4 | 30.3 | 19.6 | 70.3 | 58.3 | 68.7 | 43.2 |
| Ge―\―/―COOH | 2 | 97.9 | 95.8 | 22.6 | 11.4 | 20.3 | 10.1 | 41.8 | 12.8 | 20.3 | 7.2 | 68.3 | 43.4 | 67.4 | 44.4 |
| Ge―\―/―COOH | 3 | 96.3 | 86.2 | 21.3 | 9.3 | 18.5 | 10.2 | 30.0 | 17.4 | 24.5 | 7.6 | 74.1 | 28.9 | 53.7 | 43.7 |
| Ge―\―/―\―COOH | 4 | 96.4 | 77.6 | 22.4 | 10.6 | 14.3 | 7.0 | 36.3 | 10.3 | 22.3 | 7.0 | 66.4 | 17.7 | 46.5 | 36.2 |
| Ge―\―/(ph)―COOH | 5 | 93.4 | 75.3 | 20.5 | 9.7 | 17.8 | 3.4 | 37.6 | 8.6 | 20.3 | 6.1 | 68.8 | 17.2 | 69.4 | 38.4 |
| ph―\―COOH / Ge | 6 | 94.8 | 83.8 | 22.8 | 16.4 | 24.4 | 13.4 | 40.1 | 11.3 | 33.2 | 8.3 | 73.6 | 15.5 | 69.3 | 20.0 |
| Ge―\―/―COOCH₃ | 8 | 97.1 | 69.1 | 19.0 | 12.3 | 10.4 | 4.7 | 41.5 | 3.6 | 12.5 | 6.4 | 54.1 | 11.8 | 33.4 | 7.1 |
| Ge―\―/―CONH₂ | 10 | 97.0 | 95.2 | 24.5 | 20.6 | 23.5 | 9.6 | 46.3 | 14.3 | 19.9 | 10.3 | 74.2 | 19.9 | 68.4 | 17.5 |
| Ge―\―/(NH₂)―COOH | 17 | 97.8 | 98.4 | 24.1 | 40.2 | 20.6 | 42.3 | 40.5 | 22.5 | 31.2 | 12.4 | 70.4 | 61.2 | 66.9 | 52.4 |
| ph―\―/―COOH / Ge―\―NH₂ | 22 | 96.4 | 94.4 | 24.6 | 41.9 | 19.3 | 36.5 | 37.6 | 50.1 | 28.7 | 9.6 | 77.3 | 41.0 | 63.8 | 33.0 |

TABLE 7-continued

| Formula | Compound No. | Glucose *(1) NaOH | Glucose *(1) Electrolytic water | Mannose *(2) NaOH | Mannose *(2) Electrolytic water | Arabinose *(2) NaOH | Arabinose *(2) Electrolytic water | Isomerization ratio Ribose *(2) NaOH | Ribose *(2) Electrolytic water | Xylose *(2) NaOH | Xylose *(2) Electrolytic water | Lactose *(3) NaOH | Lactose *(3) Electrolytic water | Maltose *(3) NaOH | Maltose *(3) Electrolytic water |
|---|---|---|---|---|---|---|---|---|---|---|---|---|---|---|---|
| Ge—CH(NAc)—COOH | 26 | 92.5 | 98.3 | 23.3 | 43.2 | 18.5 | 32.7 | 32.6 | 49.4 | 39.4 | 57.7 | 72.2 | 83.8 | 65.7 | 81.0 |
| ph-Ge—CH(NAc)—COOH | 31 | 95.6 | 92.1 | 24.4 | 42.3 | 21.3 | 26.5 | 38.5 | 28.4 | 28.1 | 45.6 | 66.7 | 80.1 | 63.5 | 79.8 |
| Ge—(CH2)3—COOH | 35 | 83.2 | 86.3 | 19.4 | 8.5 | 17.8 | 6.2 | 22.8 | 1.6 | 2.1 | 2.9 | 42.0 | 20.1 | 41.1 | 8.3 |
| Ge—CH(CH3)—CH2—COOH | 36 | 79.7 | 72.4 | 14.7 | 8.0 | 12.0 | 6.4 | 18.4 | 1.3 | 4.4 | 1.6 | 47.7 | 18.8 | 38.6 | 5.6 |

*Remarks

| | Reaction time | Blank (only NaOH used) | Blank (only electrolytic water used) | Initial pH |
|---|---|---|---|---|
| (1) | 6 h | 32.3% | 2.1–3.1% | 8.0–8.53 |
| (2) | 6 h | 3.9–19.5% | 0.4–1.2% | 10.0–10.6 |
| (3) | 6 h | 34.0–38.6% | 0–0.4% | 10.0–11.0 |

EXAMPLE 4

The same isomerization test as in Example 2 was conducted with slight modifications.

That is, 200 μl of one of various saccharide solutions and 200 μl of one of various organogermanium compound solutions were placed in a small test tube. The mixture was adjusted to pH 10 with an aqueous sodium hydroxide solution, after which the tube was placed in a water bath of 80° C. for a reaction. 3 hours later, the reaction was terminated and the amount of each saccharide isomerized was determined by high-performance liquid chromatography using 7A (a column) manufactured by Shimadzu Corp.

The results are shown in Table 8.

TABLE 8

| Organogermanium compound | Galactose | Ribose | Maltose | Arabinose | Xylose | Mannose |
|---|---|---|---|---|---|---|
| | Isomerization (%) | | | | | |
| 1 | 38.67 | 27.76 | 78.91 | 20.87 | 40.66 | 37.23 |
| 8 | 40.60 | 29.60 | 80.41 | 22.22 | 33.26 | 39.18 |
| 17 | 16.38 | 27.06 | 53.84 | 7.96 | 25.88 | 16.53 |
| 22 | 19.72 | 57.98 | 49.26 | 11.49 | 31.24 | 38.20 |
| Blank | 7.60 | 2.89 | 12.59 | 2.75 | 5.59 | 12.48 |

Industrial Applicability

As is shown from the foregoing Examples, the present isomerization process is free from the problems of prior art and can isomerize a compound having an aldose structure into a compound having a ketose structure without requiring any special apparatus or any complicated operation.

This implies that an isomerized saccharose of desired concentration can be supplied, in a desired amount, to a processed food plant, for example, a plant for production of cold drink using an isomerized saccharose, by installing therein a small isomerization unit utilizing the technique of the present invention. Further, when said isomerization unit is incorporated into a processed food production line, costs associated with transportation, storage and feeding of raw materials can be reduced significantly.

Further, the present process can isomerize a compound having an aldose structure into a compound having a ketose structure in the presence or absence of an isomerization enzyme. Even when no effective isomerization enzyme is found to exist for a particular compound of aldose structure to be isomerized into a corresponding ketose structure, the present process can isomerize such a compound into a compound having a ketose structure by not resorting to the condition of heating under alkalinity (this condition is sometimes disadvantageous in isomerization ratio).

Furthermore, the present isomerization agent or accelerator effective for and used in carrying out the present process is very safe and highly stable.

We claim:

1. A process which comprises isomerizing a compound having an aldose structure into a compound having a ketose structure, by the use of an organogermanium compound or in the presence of an organogermanium compound having a structural portion represented by the following formula (I)

2. A process according to claim 1, wherein the organogermanium compound is represented by formula (II)

wherein $R_1$, $R_2$ and $R_3$, which may be the same or different, independently represent a hydrogen atom, a lower alkyl group, a substituted or unsubstituted phenyl group, a carboxyl group, a carboxyalkyl group or an amino group which is unsubstituted or substituted with appropriate group(s); $X_1$ represents a hydroxyl group, an O-lower alkyl group, an amino group or a salt represented by $OY_1$ ($Y_1$ represents a metal or a basic group-containing compound); and n represents an integer of 1 or more.

3. A process according to claim 1, wherein the organogermanium compound is represented by formula (II')

in an aqueous solution, or formula (II")

in crystal state, wherein $R_1$, $R_2$, $R_3$, $X_1$ and n are defined as above.

4. A process according to claim 2, wherein the organogermanium compound is represented by formula (III)

wherein $R_4$, $R_5$ and $R_6$, which may be the same or different, independently represent a hydrogen atom, a lower alkyl group, a substituted or unsubstituted phenyl group, a carboxyl group, a carboxyalkyl group or an amino group which is unsubstituted or substituted with appropriate group(s); and $X_2$ represents a hydroxyl group, an O-lower alkyl group, an amino group or a salt represented by $OY_2$ ($Y_2$ represents a metal or a basic group-containing compound).

5. A process according to claim 1, wherein the isomerization of a compound having an aldose structure into a compound having a ketose structure is conducted in the co-presence of an enzyme effective for that particular isomerization if such an enzyme is found to exist.

6. A process according to claim 1, wherein the isomerization of a compound having an aldose structure into a compound having a ketose structure is conducted in neutrality to alkalinity.

7. A process according to claim 1, wherein the isomerization of a compound having an aldose structure into a compound having a ketose structure is conducted in a weakly alkaline water obtained by electrolysis.

8. A process according to claim 1, wherein the isomerization of a compound having an aldose structure into a compound having a ketose structure is conducted via an interim stage in which a cis-ene-diol structure is formed.

9. A process according to claim 1, wherein the compound having an aldose structure is a monosaccharide.

10. A process according to claim 1, wherein the compound having an aldose structure is glucose and is isomerized into fructose.

11. A process according to claim 10, wherein the isomerization of glucose into fructose is conducted in the co-presence of an isomerization enzyme.

12. A process according to claim 10, wherein the isomerization of glucose into fructose is conducted in neutrality to alkalinity at a temperature of 60°–90° C.

13. A process according to claim 10, wherein the isomerization of glucose into fructose is conducted while controlling the time of isomerization reaction to control the isomerization ratio.

14. A process according to claim 10, wherein the isomerization of glucose into fructose is conducted until the ratio of isomerization into fructose reaches at least about 55%.

15. A process according to claim 11, wherein the isomerization of glucose into fructose is conducted in the co-presence of, as necessary, a metal ion required by the isomerization enzyme.

16. A process according to claim 10, wherein the isomerization of glucose into fructose is conducted in a solution which is a mixture of (1) a glucose-containing solution, (2) an organogermanium compound having a structural portion represented by the following formula and (3) an isomerization enzyme.

17. A process according to claim 16, wherein the glucose-containing solution is a syrup obtained by liquefying starch and subjecting the resulting liquid to saccharification.

18. A process according to claim 1, wherein the compound having an aldose structure is a disaccharide.

19. A process according to claim 18, wherein the compound having an aldose structure is lactose and is isomerized into lactulose.

20. A process according to claim 1, wherein the compound having an aldose structure is an oligosaccharide or a polysaccharide.

* * * * *